United States Patent [19]
Pennington

[11] Patent Number: 4,785,123
[45] Date of Patent: Nov. 15, 1988

[54] ALKYLENE OXIDES PRODUCTION USING MOLTEN NITRATE SALT CATALYSTS

[75] Inventor: B. Timothy Pennington, Sulphur, La.

[73] Assignee: Olin Corporation, Cheshire, Conn.

[21] Appl. No.: 929,552

[22] Filed: Nov. 12, 1986

[51] Int. Cl.$^4$ .............................................. C07D 301/06
[52] U.S. Cl. ..................................... 549/532; 549/533; 549/523
[58] Field of Search ................................ 549/532, 533

[56] References Cited

U.S. PATENT DOCUMENTS

| | | | |
|---|---|---|---|
| 2,366,724 | 1/1945 | Gardner | 549/533 |
| 2,530,509 | 11/1950 | Cook | 260/348.5 |
| 3,132,156 | 5/1964 | Lemon et al. | 260/348 |
| 3,641,157 | 2/1972 | Riegel et al. | 260/599 |
| 3,647,358 | 3/1972 | Greenberg | 23/2 R |
| 3,786,109 | 1/1974 | Jones | 549/533 |
| 3,850,742 | 11/1974 | Dugan et al. | 208/114 |

FOREIGN PATENT DOCUMENTS 968364 5/1975 Canada .

Primary Examiner—Norma S. Milestone
Attorney, Agent, or Firm—Dale Lynn Carlson

[57] ABSTRACT

A process for producing an alkylene oxide or mixture of alkylene oxides by a reaction which comprises reacting an alkane, an alkylene, or mixture thereof with an oxygen-containing gas in the presence of at least one molten nitrate salt.

13 Claims, No Drawings

ALKYLENE OXIDES PRODUCTION USING MOLTEN NITRATE SALT CATALYSTS

BACKGROUND OF THE INVENTION

Alkylene oxides (vicinal epoxy alkanes), and particularly propylene oxide, are very valuable and widely used chemicals. They have been polymerized with a wide variety of monomers to yield polymers which are useful in coating compositions and in the manufacture of molded articles. Alkylene oxides have also been reacted with alcohols to yield monoalkyl ethers which have utility as solvents in many commercial processes and which are useful as components for synthetic turboprop and turbojet lubricants.

There are many methods known in the art for the production of alkylene oxides and, most notably, propylene oxide. One of the oldest methods is the so-called "chlorohydrin process" which involves the reaction of chlorine and water to form hypochlorous acid which is then reacted with propylene to form propylene chlorohydrin. The propylene chlorohydrin is then dehydrohalogenated to yield propylene oxide. Another method to obtain propylene oxide hs by the liquid phase oxidation of propylene with organic peracids. Still another method involves the liquid phase oxidation of propylene with t-butyl hydroperoxide and/or ethylbenzene hydroperoxide.

The aforementioned known methods have serious disadvantages associated therewith. For example, the "chlorohydrin process" requires the use of chlorine which is relatively expensive and corrosive in nature, requiring special handling and expensive equipment. Additionally, the chlorohydrin saponification to propylene oxide consumes alkali chemicals such as caustic soda or lime, producing a large aqueous waste stream containing chloride salts, which require costly treatment prior to discharge from the plant. The oxidation of propylene with peracids is a potentially dangerous operation and expensive equipment is needed to guard against potentially explosive hazards when working with the peracids. Another disadvantage of this method is the high cost of peracids. The t-butyl hydroperoxide and ethylbenzene hydroperoxide processes have the disadvantages of being capital-intensive, multi-step, rather complicated processes. Furthermore, these processes require co-feedstocks of isobutane or ethylbenzene, thus constraining the practical utility of the processes for propylene oxide manufacture.

Another method which has received considerable attention in the literature is the direct oxidation of hydrocarbons with an oxygen-containing gas. This method suffers from the disadvantage that it is not specific for the production of alkylene oxides but produces a variety of other compounds including acids, esters, ethers, and oxides of carbon including carbon monoxide and carbon dioxide. The reaction does, however, possess two attributes which recommend it highly for commercial utilization, i.e., inexpensiveness of starting materials and simplicity of operation. It is primarily for these reasons that much attention in recent years has been directed to improvements in methods for the production of alkylene oxides from the direct oxidation of hydrocarbons even though the producer must necessarily contend with the concurrent production of a variety of undesired products.

By way of illustration, the prior art methods which attempted to produce propylene oxide by the oxidation of propane such as that disclosed in U.S. Pat. No. 2,530,509, assigned to Linde Air Products Company, were only partially successful. The majority of the prior art methods used conventional vertical columns and differed from each other by variations in lengths and diameter of the column, temperature, pressure, etc. However, all of these methods suffered one common disadvantage—the temperature of the reactants varied throughout the length of the cOlumn.

The temperature variations are easily explained since the oxidation reactions are exothermic and the amount of heat evolved differs with each reaction which is taking place. Thus, at various increments along the tube, conditions existed which favored the direction of the oxidation to products other than propylene oxide. These prior art methods necessitated the use of elaborate and expensive cooling apparatus.

Further developments in the art constituted attempts to maximize the desired olefin oxide production while minimizing by-product formation. For example, U.S. Pat. No. 3,132,156, assigned to Union Carbide Corporation, discloses the vapor phase oxidation of saturated aliphatic hydrocarbons to olefin oxides. The method described in this '156 patent is said to provide enhanced olefin oxide production as high as 46.2 lbs per 100 lbs of $C_3$ consumed which calculates to be about 33 percent (molar) selectivity. While this level of selectivity constituted an improvement, it remains less than might be desired from a commercial standpoint. Likewise, Canadian Patent No. 968,364, assigned to Union Carbide Corporation, discloses the indirect oxidation of olefin oxides via the oxidation of methanol to a free radical intermediate which in turn, epoxidizes the olefin. However, the indirect oxidation method disclosed in the Canadian '364 patent has the disadvantage of requiring the use of a solvent together with subsequent solvent separation step(s). Accordingly, new methods of producing olefin oxides that combine enhanced selectivity with a simple, inexpensive process would be highly desirable.

SUMMARY OF THE INVENTION

In one aspect, the present invention relates to a process for producing an alkylene oxide or mixture of alkylene oxides by a reaction which comprises reacting an alkane, an alkylene, or mixture thereof with an oxygen-containing gas in the presence of at least one molten nitrate salt. Preferably, this process comprises the method of bubbling the gaseous reactants through a reactor containing the molten nitrate salt(s).

In another aspect, the present invention relates to another embodiment of such a process wherein the reaction is conducted in the additional presence of a suitable metallic co-catalyst such as elemental metals (preferably palladium), or their oxides or hydroxides (particularly sodium hydroxide), or mixtures thereof.

DETAILED DESCRIPTION OF INVENTION

Several factors will affect the reactant conversion to alkylene oxide and the selectivity of alkylene oxide production vis-a-vis by-product production in accordance with the process of the present invention. These factors include, for example: the contact time of the molten salt with the oxygen-containing gas, the temperature of the reactor product gases, the molten salt temperature, the molten salt composition, the feed gas temperature, the feed gas composition, and the feed gas pressure.

The oxygen-containing gas useful as a reactant in the present invention can be any such gas. Typically, air is employed as the oxygen-containing gas based upon its ready availability. However, other oxygen-containing gases such as pure oxygen may be employed if desired, and the use of oxygen is expected to be preferred in a commercial setting.

The alkylene compound or olefin useful in the present invention can be broadly defined as an epoxidizable, olefinically-unsaturated hydrocarbon compound having from 3 to 22 carbon atoms. This definition is intended to include terminal olefins selected from the group consisting of monofunctional and difunctional olefins having the following structural formulas respectively:

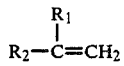

where $R_1$ is hydrogen or an alkyl chain, straight or branched, having 1 to 20 carbon atoms and $R_2$ is an alkyl chain, straight or branched, having 1 to 20 carbon atoms; and

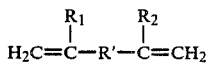

wherein $R_1$ and $R_2$ are hydrogen atoms or alkyl chains having 1 to 10 carbon atoms and $R'$ is from 2 to 10 methylene groups. The definition also includes cyclic olefins and internal olefins. The ring portions of the cyclic olefins can have up to 10 carbon atoms and one unsaturated bond and can be substituted with one or two alkyl radicals having 1 to 10 carbon atoms. The cyclic olefins are typically represented by the following structural formula:

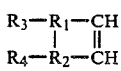

wherein $R_1$ and $R_2$ are alkylene radicals having 1 to 4 carbon atoms and $R_3$ and $R_4$ represent hydrogen atoms, or one or two alkyl radicals, straight or branched chain, having 1 to 10 carbon atoms. The internal olefins are represented by the following structural formula:

wherein $R_1$ and $R_2$ are straight chain or branched chain alkyl radicals having 1 to 10 carbon atoms.

The alkanes, alkylenes, and mixtures thereof useful as reactants in accordance with the present invention generally have up to, but do not exceed, about 22 carbon atoms per molecule, preferably not more than 12 carbon atoms per molecule. When a straight-chain molecule is employed, it is more preferred that such molecule not have more than five carbon atoms. When a cyclic compound is used, it is more preferred that the cyclic compound not have more than 12 carbon atoms per molecule. Illustrative reactants include, propane, propylene, isobutane, butane, cyclohexene, and mixtures thereof. A preferred reactant within this group is propylene or a mixture of propylene and propane based upon their commercial availability.

Representative other alkylene compounds or olefins are butene-1, butene-2, isobutylene, pentene-1, hexene-1, pentene-2, cyclopentene, and cyclooctene. Other representative olefins are 2-methylbutene-1, 3-methylbutene-1, heptene-1, octene-1, hexene-2, hexene-3, octene-2, heptene-3, pentadecene-1, octadecene-1, dodecene-2, 2-methylpentene-2, tetramethylethylene, methylethylethylene, cyclobutene, cycloheptene, 2-methylheptene-1, 2,4,4-trimethylpentene-1, 2-methylbutene-2, 4-methylpentene-2, and 2-ethyl-3-methylbutene-1.

The olefin and/or alkane gas is preferably preheated to prevent condensation in the line delivering this gas to the reactor. Alternatively, both the oxygen-containing gas and the olefin and/or alkane gas (collectively referred to herein as "the feed gases") can be preheated to prevent condensation in all of the feed gases. However, in the absence of preheat, the molten nitrate salt will rapidly heat the feed gases up to reaction temperature. If the feed gas is preheated, it preferably is maintained at at least about 100° C. in the feed gas line(s).

The molten nitrate salt(s) is generally maintained at a temperature sufficient to keep the salt(s) in a molten condition. Preferably, the temperature is maintained between about 135° C. (275° F.) and about 600° C. (1,000° F.) during the reaction in accordance with the present invention. The specific temperature selected is based upon the melting point of the particular molten nitrate salt chosen. For example, mixtures of molten lithium and potassium nitrate can be suitably employed at a temperature as low as about 280° F., and hence, this temperature may be employed when using lithium nitrate. In the selection of a suitable molten nitrate salt bath temperature, it is important to choose a temperature below the thermal decomposition temperature for the particular molten nitrate salt chosen. In addition, it is important to maintain a sufficient isotherm across the molten nitrate salt bath so as to avoid crust formation of the nitrate salt in the bath. Such a crust formation in the nitrate salt bath can cause localized overheating of gases trapped by the crust in the bath and an associated "runaway" oxidation reaction due to overheating of the gases in the bath. In order to maintain a bath isotherm, constant stirring of the molten nitrate salt bath is preferred. Alternatively, the molten salt can be circulated by conventional means, such as the use of internal draft tubes or external pumping loops.

The nitrate salt used may be any one of the alkali or alkaline earth nitrates such as lithium, sodium, potassium, rubidium, cesium, magnesium, calcium, strontium, or barium or mixtures thereof. In addition, the nitrate salts can be used in mixtures with other salts such as chlorides, bromides, carbonates, sulfates, and phosphates. Generally, the content of the other salt(s), when present, should be restricted to less than 60 percent by weight based upon the weight of the total melt and in most cases their contents should not exceed about 25 percent of the total melt.

The ratio of alkane and/or alkylene to oxygen in the oxygen-containing gas in the reactor can vary over a wide range. However, in accordance with the present invention, it has now been found that enhanced selectivity of alkylene oxide product is achieved by maintaining a relatively low amount of oxygen relative to the amount of alkane/alkylene fed into the reactor. For example, when reacting propylene with oxygen in a molten potassium nitrate salt column at atmospheric pressure, a ratio of between about 1 and about 20 volume percent of oxygen, e.g., about 5 volume percent oxygen to about 95 volume percent propylene has been found to provide an enhanced selectivity of propylene oxide. When using air as the oxygen-containing gas, it is preferably employed in an amount of between about 5 and about 75 volume percent based upon the total amount of air plus propylene employed in the reaction. Another consideration in the selection of the amount of propylene or other alkylene to use as a feed is the high partial pressure of the alkylene which in high concentrations can cause thermal cracking of the alkylene reactant itself. Therefore, when conducting the oxidation reaction at an elevated pressure, viz 75 psig, it is preferred to "cut" the amount of propylene in the illustrative example to 75 volume percent and utilize an inert blanket ("diluent") gas, such as nitrogen, to provide the remaining 20 volume percent of feed gas. Alternatively, the diluent gas may be comprised of mixtures of oxidation by-product gases such as acetaldehyde, methane, and carbon dioxide, generally readily obtainable from the propylene oxide purification operations downstream of the molten salt reactor.

In the selection of the ratio of the volume of oxygen-containing gas relative to the volume of alkylene/alkane employed in the reaction mixture, the range of ratios which might pose a flammability hazard should be avoided, as is well known. For example, when utilizing an air/propylene reactant mixture at atmospheric pressure, the range of below 12 volume percent of propylene based upon total air plus propylene should be avoided.

In accordance with the present invention, it has been found that the addition of elemental metal or their oxides or hydroxides as a co-catalyst in conjunction with the molten nitrate salt makes it possible to lower the reaction temperature for the particular nitrate salt selected and/or enhance the selectivity or conversion to the desired olefin oxide. For example, it has been found in accordance with the present invention that although a temperature of about 380° C. is normally required when reacting propylene with air to produce propylene oxide in the presence of sodium nitrate at atmospheric pressure, the temperature can be reduced to 350° F. provided that a co-catalyst of palladium on alumina is employed in conjunction with the molten salt. The use of a metal co-catalyst is preferred when the reaction is conducted at atmospheric pressure. At superatmospheric pressure a sodium hydroxide co-catalyst has been found to be particularly advantageous. If used, the co-catalyst is generally employed in a catalytically effective amount, generally in an amount of less than about 5 (preferably between about 0.5 and about 5) weight percent based on the total amount of co-catalyst plus molten salt catalyst.

The molten salt bath in which the elemental metal or their oxides or hydroxides co-catalyst, if used, is suspended or dispersed helps to maintain the co-catalyst at a constant desired temperature or isotherm. The maintenance of the co-catalyst in such an isotherm makes it possible to reduce or avoid the problems of co-catalyst de-activation that might otherwise be encountered in a non-isothermal system due to overheating of the co-catalyst itself or due to thermal degradation of product to a tarry by-product which can coat, and thus de-activate, the catalyst.

The molten salt(s), in addition to functioning as a catalyst and as an isothermal medium for any co-catalyst, also serve as a temperature regulator. More specifically, the molten nitrate salt(s) have a high heat absorption capacity, enabling them to absorb large quantities of heat during the exothermic oxidation reaction while maintaining an essentially constant reaction temperature and thereby preventing a runaway reaction. The absorbed heat of reaction from this exothermic oxidation may be employed in the process of the present invention to help maintain the molten salt in a molten state and/or to heat the gaseous reactants to reaction temperature.

In a preferred embodiment of the present invention, a mixture of potassium and sodium molten nitrate salts is employed comprising between about 20 and about 80 weight percent of sodium nitrate, preferably between about 45 and about 65 weight percent of sodium nitrate based upon the total amount of sodium nitrate and potassium nitrate in the molten salt mixture.

The preferred method of contacting the gaseous reactants in the presence of the molten nitrate salt is by bubbling the reactants through a bath of the molten salt. If the gaseous reactants are bubbled into the bottom of the bath or column containing the molten nitrate salt, the contact time of the reactants with the molten salt catalyst is equal to the "rise time" of the reactants through the bath or column. Thus, the contact time can be increased by increasing the length of the molten nitrate salt bath column. An alternate method of contacting the gaseous reactants in the presence of the molten salt would be to pass the gaseous reactants through a reactor countercurrently to a spray or mist of the molten salt. This latter method provides for enhanced surface area contact of the reactants with the molten salt. Still another method of contacting the gaseous reactants with molten salt would be to inject the reactants into a circulating stream of molten salt, wherein the kinetic energy of both streams is utilized to provide intimate mixing through the application of nozzles, mixers, and other conventional equipment. These methods are only illustrative of types of reaction systems which may be employed in the practice of this disclosure. Other conventional methods of gas-liquid contact in reaction systems may also be employed.

The alkane and or alkylene feed gas(es) can be passed into the molten nitrate salt-containing reactor using a separate stream (e.g. feed tube) from the stream delivering the oxygen-containing gas to the reactor. Alternatively, the reactant gases can be fed into the reactor together in a single stream. In a preferred embodiment of the present invention, two co-axially-mounted feed gas tubes are emPloyed. The co-axial mounting of the feed gas tubes has been found to reduce or minimize the back-up of molten salt into an unpressurized feed tube if pressure is temporarily lost in either (but not both) feed tube. Mixing of the gaseous reactants prior to, or at the point of, the gas(es) inlet into the reactor is desired in order to facilitate the oxidation reaction. Mixing is suitably accomplished using an impingement mixer or sparger tube.

The feed gas is preferably bubbled into the molten nitrate salt-containing reactor using a sparger. If used, the sparger is preferably positioned in the molten nitrate salt to a sparger exit port depth of between about 2 and about 1000 centimeters, preferably between about 10 and about 200 centimeters, depending upon the size of the reactor utilized and the overall depth of the molten salt in the reactor. Alternatively, the gas can be fed directly into the bottom of the reactor by a feed tube. The feed gas tubes are preferably co-axially mounted so that in the event of a loss of pressure in either gas tube, the gas in the other tube will maintain a sufficient pressure to keep the molten salt from backing up into the unpressurized feed gas tube.

This process can be run in a batchwise or continuous operation, the latter being preferred. The order of introduction of the reactants is determined by the operator based on what is most safe and practical under prevalent conditions. Generally, the desirability of avoiding flammable gas mixtures throughout the reaction and subsequent product separation systems will dictate the desired procedures.

The process can be carried out by feeding a mixture of alkylene, inert gas, and oxygen into a reaction vessel containing molten nitrate salt. The reaction vessel can be glass, glass-lined metal, or made of titanium. For example, a glass-lined stainless steel autoclave can be used, although, even better from a commercial point of view, is an unlined type 316 stainless steel atoclave (as defined bY the American Iron and Steel Institute). A tubular reactor made of similar materials can also be used together with multi-point injection to maintain a particular ratio of reactants. Other specialized materials may be economically preferred to minimize corrosion and contamination of the molten salt and products, or to extend the useful life of the reaction system.

Some form of agitation of the molten salt(s)/feed gas mixture is preferred to avoid a static system and insure the homogeneity of the molten salt, agitation helps prevent crust formation of the salt(s) at the head gas/salt interface in the reactor. This can be accomplished by using a mechanically stirred autoclave, a multi-point injection system, or a continuous process, e.g., with a loop reactor wherein the reactants are force circulated through the system. Sparging can also be used. In the subject process, it is found that increased rates of reaction are obtained by good gas-liquid contact provided by agitation of the molten salt/gas mixture.

The process of the present invention is suitably carried out at atmospheric, subatmospheric or superatmospheric pressure. Preferably, the process is effected at superatmospheric pressures of up to about 100 atmospheres, preferably between about 1 atmosphere and about 40 atmospheres, more preferably between about 1 atmosphere and about 25 atmospheres.

It is to be understood that by-products are also produced during the reaction. For example, some dehydrogenation of the feed is also effected, particularly at higher temperatures within the hereinabove noted temperature range, and therefore, the reaction conditions are generally controlled to minimize such production. The separation of the resulting by-products in order to recover the desired product may be effected by a wide variety of well-known procedures such as: absorption in water followed by fractional distillation, absorption, and condensation.

The following examples are intended to illustrate, but in no way limit the scope of, the present invention.

EXAMPLE 1

Atmospheric Pressure Reaction of Propylene and Air in a Molten Salt Mixture of 55% Sodium Nitrate and 45% Potassium Nitrate A six liter cylindrical stainless steel flanged-top reactor approximately 76 cm deep and 10 cm in diameter was filled with 5,500 g $NaNO_3$ and 4,500 g $KNO_3$. The salt mixture was melted and brought up to 454° C. by use of externally wrapped electrical resistance heating coils. Propylene at the rate of 235 cc/min was sparged into the melt through a porous metal sparging element submerged at a depth of 51 cm in the molten salt. Air at the rate of 715 cc/min was sparged into the melt through a ⅛ inch stainless steel line, the end of which was located directly beneath the propylene sparger, so that the air and propylene contacted each other. The sparging was continued for 30 minutes with the gases exiting the reactor at atmospheric pressure. The gas exiting the reactor passed through a trap for condensible substances and through a gas sample cylinder ("sample bomb") in line after the trap. After completing the reaction, the trap was found to contain about 0.5 ml of a liquid which was analyzed by gas chromatography methods and found to be about 75 percent water and 25 percent water soluble organics. The water soluble organics consisted mainly of methanol (about 50 percent), formaldehyde, allyl alcohol, acetaldehyde, propylene oxide, and acetone in order of descending concentration. The gas sample in the cylinder was analyzed by gas chromatography and gas chromatogra-phy/mass spectrometry and was found to contain propylene oxide, acetaldehyde, ethylene, and methanol, along with carbon dioxide as the major components. The propylene conversion was calculated from gas chromatography data to be 15.4 percent. The selectivity of propylene to the various products was calculated to be as follows:

TABLE I

| Compound | Molar Selectivity (%) |
|---|---|
| Propylene Oxide | 26.2 |
| Acetaldehyde | 23.5 |
| $CO_2$ | 19.6 |
| Ethylene | 15.0 |
| Methanol & Formaldehyde | 5.5 |
| Allyl Alcohol | 3.5 |
| Butene Isomers | 2.6 |
| Acetone | 2.1 |
| 1,5-Hexadiene | 1.3 |
| 4-Methyl-1,3-Oxolane | 0.4 |
| Other | 0.3 |

EXAMPLE 2

Atmospheric Pressure Reaction of Propylene Preheated Before Entering the Reactor and Air in a Molten Salt Mixture of 60% Sodium Nitrate and 40% Potassium Nitrate A similar reactor as in EXAMPLE 1 was charged with 6 Kg $NaNO_3$ and 4 Kg $KNO_3$. The salt mixture was melted and brought up to 454° C. Propylene at 500 cc/min was fed in as in EXAMPLE 1, except that the propylene was passed through a preheater tube immediately before entering the molten salt reactor to attain a temperature of 220°-225° C. Air at the rate of 800 cc/min was sparged into the reactor as in EXAMPLE 1 without preheating. The gases exited the reactor at atmospheric pressure through a cold trap for condensible substances followed by a sample cylinder for collecting gas samples. At the end of the run, which lasted one hour, 9.1 grams of liquid was collected from the trap. This liquid was found to contain about 50 percent water and 50 percent water soluble organics, including in order of abundance, acetaldehyde, propylene oxide, methanol, formaldehyde, allyl alcohol, 1,3-propylene glycol, acetone, acrolein, and hydroxyacetone. The gas sample was found to contain in order of abundance, unreacted propylene, carbon dioxide, ethylene, acetaldehyde, propylene oxide, and other components in lesser amounts. The conversion of propylene was calculated to be 15.6 percent. The selectivity calculations are given in TABLE II below.

TABLE II

| Compound | Molar Selectivity (%) |
| --- | --- |
| $CO_2$ | 30.3 |
| Acetaldehyde | 24.2 |
| Propylene Oxide | 17.7 |
| Ethylene | 14.8 |
| Methanol | 6.3 |
| Formaldehyde | 4.0 |
| Allyl Alcohol | 4.3 |
| Acetone | 3.5 |
| Acrolein | 2.3 |
| 1,5-Hexadiene | 1.4 |
| Other | 1.5 |

The nitrate salt mixture was analyzed for carbonate, hydroxide, and nitrite content before and after a series of runs like those described in EXAMPLES 1 and 2. If the salt were reacting directly to produce the observed oxidation, the amounts of the three ions would be expected to rise rapidly until all the nitrate was consumed. Analysis of a 10,000 gram 60 percent by weight sodium nitrate-40 percent by weight potassium nitrate salt mixture held at 454° C. for several days before beginning any reactions between propylene and air showed 6, 7, and 3123 ppm of carbonate, hydroxide, and nitrite in that order. After 30 hours of reaction between propylene and air or oxygen at atmospheric pressure at 454° C., the salt analysis showed 54, 29, and 3416 ppm of carbonate, hydroxide, and nitrite in that order. These results indicate that a small amount of salt degradation occurred, but that the amount of degradation is several hundred times too low for the salt to be reacting directly to produce the propylene oxidation products.

COMPARATIVE EXAMPLE A

Comparative Example of Direct Oxidation of Propylene and Air in the Absence of Molten Salt at Ambient Pressure This Comparative Example was run to test the efficacy of directly reacting propylene and air at 454° C. in the absence of molten nitrate salt.

This experiment was conducted as follows: The flanged top of the reactor used in EXAMPLE 2 was removed and a one liter reactor bomb with ⅛ inch stainless steel tubing coiled around it was immersed in a molten salt bath at 454° C. Propylene at 500 cc/min and air at 800° C./min were fed into the reactor bomb through ⅛ inch stainless steel tubing. The gas exited the bomb through ⅛ inch stainless steel tubing connected to a cold trap and followed by a gas sample bomb. The exit gas pressure was atmospheric. The gases were allowed to flow for one hour and then the contents of the trap and the gas sample bomb were collected for analysis. The liquid in the trap was found to contain about 90 percent water, but also formaldehyde, allyl alcohol, acrolein, and acetaldehyde, along with traces of other components. The exit gas was found to contain unreacted propylene, carbon dioxide, acrolein, and lesser amounts of ethylene, 1,5-hexadiene, acetaldehyde, 1,3-butadiene, butene isomers, ethanol, allyl alcohol, $C_6H_{10}$, benzene, and only a trace of propylene oxide. The conversion of propylene was calculated to be 8.1 percent. The selectivity of propylene to propylene oxide and the various by-products was calculated. These selectivity calculations are given in TABLE III below.

TABLE III

| Compound | Molar Selectivity (%) |
| --- | --- |
| $CO_2$ | 80.6 |
| Acrolein | 9.4 |
| 1,5-Hexadiene | 3.9 |
| Ethylene | 1.0 |
| 1,3-Butadiene | 1.4 |
| Formaldehyde | 1.2 |
| Acetaldehyde | 0.8 |
| Allyl Alcohol | 0.5 |
| Benzene | 0.5 |
| Propylene Oxide | 0.1 |
| Other | 0.6 |

A comparison of the results at ambient pressure given in TABLE III for the direct oxidation of propylene with the results given in TABLE II for the mOlten salt oxidation shows the clear superiority of the molten salt method in terms of percent conversion of propylene to propylene oxide plus other products (15.6 percent versus 8.1 percent) and propylene oxide selectivity (17.7 percent versus 0.1 percent).

EXAMPLE 3

Atmospheric Pressure Reaction of Cyclohexene and Air in a Molten Salt Mixture of 60% Sodium Nitrate and 40% Potassium Nitrate A two-liter reactor, approximately 26 cm deep and 10.1 cm wide, was charged with a salt mixture consisting of 1.2 Kg $NaNO_3$ and 0.8 Kg $KNO_3$. The salt mixture was melted using external electrical resistance heating and was heated to 400° C. The melt was stirred using a magnetic stirrer. Cyclohexene at the rate of one ml liquid per minute at 84° C. was pumped into a feed line swept out by nitrogen flow at the rate of 520 cc/min. The cyclohexene was carried by the nitrogen into the molten salt through a sparger immersed 10.1 cm deep into the melt. Air at a flow rate of 520 cc/min was sparged through a separate line situated just below the cyclohexene feed point. After 41 minutes, the flows were stopped and the product streams from the cold trap and gas sample bomb (placed in-line as used in EXAMPLE 1 above) were analyzed. The gas sample bomb contained 94 percent air and nitrogen and about 5 percent unreacted cyclohexene with a small amount of carbon dioxide and traces of other gases. The trap sample was found to contain cyclohexene oxide, 1-cyclopentene-1-carboxyaldehyde, 2-cyclohexene-1-one-4-ol, 2-cyclohexene-1-one, as the major products. The conversion as calculated from gas chromatography data was 3.6 percent. The selectivities of propylene were calculated and are given in Table IV below.

TABLE IV

| Compound | Molar Selectivity (%) |
| --- | --- |
| $CO_2$ | 3.0 |
| Cyclohexene Oxide | 25.1 |
| 1-Cyclopentene-1-carboxyaldehyde | 21.6 |
| 2-Cyclohexene-1-one-4-ol | 13.9 |
| 2-Cyclohexene-1-one | 7.1 |
| Dicyclohexene | 6.4 |
| 2,4-Hexadienal | 4.3 |
| $C_5H_{10}$ Isomers | 4.2 |
| 2-Cyclohexene-1-ol | 4.1 |
| Other | 10.3 |

EXAMPLE 4

Atmospheric Pressure Reaction of Isobutane Preheated Before Entering the Reactor and Oxygen in a Molten Salt Mixture of 55% Sodium Nitrate and 45% Potassium Nitrate

Using the same reactor and salt mixture as used in EXAMPLE 1, isobutane, after being preheated to 240° C., was sparged into the molten salt at 454° C. through the same sparger as used in EXAMPLE 1 placed at a depth of 51 cm into the melt. The flow rate of isobutane was 810 cc/min. Oxygen was fed in through a separate line (in a fashion analogous to that used for air in EXAMPLE 1) at a flow rate of 220 cc/min. After running the experiment for 45 minutes, the flows were stopped and the contents of the cold trap and gas sample bomb (placed in the product stream lines as in EXAMPLE 1 above) were analyzed. The cold trap was found to contain 5.0 ml of condensate analyzed as 70 percent water, with the balance mainly methanol and 1,2-isobutylene glycol. The gas sample was found to contain 90 percent isobutane, 3.5 percent oxygen, 1.6 percent carbon dioxide, and the balance was various reaction products including isobutylene oxide, propylene, and acetone as major products. The conversion of isobutane was calculated by gas chromatography to be 7.2 percent. The selectivities of various products were calculated and are given in TABLE V below.

TABLE V

| Compound | Molar Selectivity (%) |
|---|---|
| $CO_2$ | 15.1 |
| Isobutylene Oxide | 31.2 |
| Propylene | 29.9 |
| Acetone | 8.7 |
| Methanol | 4.4 |
| 1,2-Isobutylene Glycol | 3.4 |
| Propylene Oxide | 1.7 |
| Ethylene | 0.5 |
| 2-Methylacrolein | 0.3 |
| Other | 4.8 |

EXAMPLE 5

Atmospheric Pressure Reaction of Isobutylene and Air in a Molten Salt Mixture of 60% Sodium Nitrate and 40% Potassium Nitrate

Using the same reactor and salt mixture as in EXAMPLE 3, 223 cc/min of isobutylene was first passed through a preheater to elevate the temperature of the gas to 178° C. and then sparged through the molten salt. Air at a flow rate of 740 cc/min was fed in through a separate line as in EXAMPLE 3. The experiment was allowed to proceed for 30 minutes. The contents of the gas sample bomb showed that the major products were acetone, isobutylene oxide, and propylene, formed in about a 4:2:1 ratio, respectively. The condensate was not analyzed.

EXAMPLE 6

Palladium on Alumina Co-Catalyzation With Molten Nitrate Salt ($NaNO_3$/$KNO_3$)Mixture at Atmospheric Pressure

In order to determine the efficacy of palladium on alumina as a co-catalyst in a molten nitrate salt bath at atmospheric pressure, the following test was conducted.

For purposes of this test, two gas compositions were employed, Gas Composition 1 containing 75 percent air and 25 percent propylene and added to the reactor at a flow rate of 1000 cc per minute; and Gas Composition 2 containing 12 percent pure oxygen and 88 percent propylene and added to the reactor at a flow rate of 850 cc per minute.

To a reactor analogous to that described in EXAMPLE 1 was charged a molten salt mixture as described in EXAMPLE 1. Either Feed Gas 1 or Feed Gas 2 was added to the reactor, as more fully identified in TABLE VI below. The molten salt temperature was maintained at either 350° C. or 400° C., as identified in TABLE VI below. Sparging of the selected gas composition into the reactor was made at the above-identified flow rates and conducted for 30 minutes with product and by-product gases exiting the reactor at atmospheric pressure. The product gases were analyzed for conversions and molar selectivity. These are identified in TABLE VI below.

TABLE VI

COMPARISON OF ATMOSPHERIC PRESSURE MOLTEN SALT CO-CATALYSIS WITH PALLADIUM ON ALUMINA VERSUS NO CO-CATALYST

| Run # | Co-Catalyst | Salt Temp. (°C.) | Feed Gas* | Conversions $C_3$ (%) | $O_2$ (%) | Selectivity (%) $CO_2$ | Hydrocarbons | Formaldehyde | Methanol | Acetaldehyde | Propylene oxide | Other |
|---|---|---|---|---|---|---|---|---|---|---|---|---|
| 1 | None | 350 | 1 | 0 | 0 | 0 | 0 | 0 | 0 | 0 | 0 | 0 |
| 2 | None | 350 | 2 | 0 | 0 | 0 | 0 | 0 | 0 | 0 | 0 | 0 |
| 3 | None | 400 | 1 | 20.9 | 89.5 | 35.0 | 5.8 | 4.6 | 2.2 | 17.2 | 17.8 | 17.3 |
| 4 | None | 400 | 2 | 12.5 | 100 | 31.0 | 10.2 | 3.1 | 0.6 | 18.7 | 18.5 | 17.5 |
| 5 | .3% Pd on alumina | 350 | 1 | 0 | 0 | 0 | 0 | 0 | 0 | 0 | 0 | 0 |
| 6 | .3% Pd on alumina | 350 | 2 | 0.2 | 1.9 | 21.9 | 1.3 | 12.4 | 0 | 22.1 | 27.9 | 14.4 |
| 7 | .3% Pd on alumina | 400 | 1 | 21.8 | 61.4 | 30.4 | 7.4 | 7.6 | 4.1 | 18.9 | 19.7 | 12.0 |
| 8 | .3% Pd on alumina | 400 | 2 | 13.4 | 100+ | 29.4 | 10.4 | 6.3 | 2.0 | 19.8 | 20.0 | 12.1 |

*(1) 25% $C_3H_6$/75% air; flow rate 1000 cc/minute
(2) 88% $C_3H_6$/12% oxygen; flow rate 850 cc/minute The results as provided in TABLE VI above indicated that palladium on alumina is an effective co-catalyst in conjunction with molten nitrate salt in enhancing the molar selectivity of propylene oxide production, as compared to the use of molten nitrate salt alone when carrying out the reaction with a propylene rich feed (Gas Composition 2). For example, at 350° C. Run 6 employing 0.3 weight percent palladium on alumina provided a propylene oxide selectivity of 27.9 percent, the highest seen at atmospheric pressure. In Run 2 wherein no palladium catalyst was employed there was no reaction. At 400° C. (compare Run 8 with Run 4 of TABLE VI) a slight improvement (20.0 percent propylene oxide selectivity versus 18.5 percent propylene oxide selectivity) resulted.

Other potential co-catalysts, such as vanadium pentoxide on alumina, were found not to enhance propylene oxide selectivity at atmospheric pressure.

When a similar comparison was conducted under pressure of 75 psig, it was found that no co-catalyst was needed. Indeed under pressure, palladium on alumina provided decreased selectivity of propylene oxide.

EXAMPLE 7

Elevated Pressure (75 psig) Reaction of Propylene and Air in Molten (NaNO$_3$/KNO$_3$) Salt A two liter cylindrical stainless steel autoclave reactor capable of withstanding 5,000 psia at 100° C. was filled with 1320 g NaNO$_3$ and 880 g KNO$_3$ The salt mixture was melted and brought up to 350° C. by use of an external electrical resistance heater. Propylene at the rate of 1000 cc/min was sparged into the melt in a ⅛ inch stainless steel inner tube of a pair of concentric tubes and air at the rate of 1000 cc/min was sparged through the outer ¼ inch tube. The gases met and mixed inside a porous metal sparging element that was attached to the outer of the concentric tubes just before exiting the sparger and entering the molten salt. The reactor pressure was maintained at 75 psig by means of a backpressure regulator. The feed gas pressure was 20 psig in excess of the backpressure regulator setting in order to get a continuous flow through the reactor system. The molten salt temperature was brought up to 385° C. gradually over a period of several hours while continuing the sparging of the feed gases. All conditions were held the same for one hour. The gas exiting the reactor passed through an ice water trap for condensible substances and through a gas sample cylinder in the line after the trap. After completing the reaction, the trap was found to contain only a trace of liquid (less than 0.1 ml). The gas sample in the cylinder was analyzed by three different gas chromatography methods and was found to contain propylene oxide, acetaldehyde, formaldehyde, and carbon dioxide as the major products.

The conversion of propylene was calculated to be 2.5 percent and the oxygen conversion was calculated to be 17.6 percent. The selectivity of propylene to the various products was calculated, and these results are given in TABLE VII below.

TABLE VII

| Comparison | Molar Selectivity (%) |
| --- | --- |
| Propylene Oxide | 41 |
| Acetaldehyde | 20 |
| Formaldehyde | 11 |
| Carbon Dioxide | 16 |
| Carbon Monoxide | Trace |
| Acrolein | 3 |
| Ethylene, Ethane, and Methane | 3 |
| Acetone | 2 |
| Allyl Alcohol | 2 |
| 1,5-Hexadiene | 1 |
| Other | 1 |

COMPARATIVE EXAMPLE B

Vapor Phase Oxidation of Propylene With Air at Elevated Pressure (75 psig)

A 250 ml gas sample cylinder fitted with a ¼ inch gas feed line at one end and a ¼ inch exit line at the other end was immersed into a molten nitrate salt bath at 360° C. Propylene at a feed rate of 1000 cc/min and air at a feed rate of 1000 cc/min were mixed and passed through the 250 ml cylinder immersed in molten salt. The system was maintained at 75 psig by use of a backpressure regulator. The gas exiting the backpressure regulator passed through an ice water trap for condensible substances and through a gas sample cylinder in line after the trap. After a one hour reaction time, the trap was found to contain 14.5 ml of liquid which subsequent analysis showed to be about 80 percent water. The pH of the liquid was found to be about 3.0 which indicated the presence of organic acids such as formic acid and acetic acid. The water soluble organics consisted mainly of methanol, formaldehyde, allyl alcohol, acetaldehyde, propylene oxide, acetone, and traces of organic acids. The reactor exit gases were analyzed by gas chromatography and found to contain propylene oxide, acetaldehyde, ethylene, ethane, methane, methanol, formaldehyde, along with carbon dioxide and large amounts of carbon monoxide as the major products. The conversion of propylene was calculated to be 12.6 percent and the oxygen conversion was calculated to be 89 percent. The molar selectivity of propylene to the various products is given in TABLE VIII below:

TABLE VIII

| Compound | Molar Selectivity (%) |
| --- | --- |
| Propylene Oxide | 20 |
| Acetaldehyde | 15 |
| Formaldehyde | 5 |
| Carbon Dioxide | 13 |
| Carbon Monoxide | 15 |
| Ethylene, Ethane, and Methane | 8 |
| Methanol | 3 |
| Ethanol | 1 |
| Butene Isomers | 5 |
| Acrolein | 4 |
| Acetone | 2 |
| Allyl Alcohol | 2 |
| 1,5-Hexadiene | 5 |
| Other | 2 |

A comparison of the results of this comparative example to the results given in EXAMPLE 8 shows that the vapor phase oxidation provided better conversion of propylene (12.6 percent versus 2.5 percent) but poorer selectivity 20 percent propylene oxide selectivity versus 41 percent) as compared to the molten nitrate salt catalyzed oxidation of EXAMPLE 8. Enhanced selectivity is considered to be the most important of these two parameters.

EXAMPLE 9

Elevated Pressure (75 psig) Reaction of Propylene With Air in Molten Nitrate Salt Mixture With NaOH Present To the same autoclave reactor with the same salt mixture as in EXAMPLE 7 was added 50 grams NaOH. All other conditions were the same as in the pressurized reactor example and the reaction was carried out in an analogous fashion. After completing one hour of reaction at 380° C., the condensible trap was found to be empty. The exit gas analysis showed a propylene conversion of 1.1 percent and an oxygen conversion of 12.5 percent. The selectivity of propylene to the varous products was calculated and are given in TABLE IX below.

TABLE IX

| Compound | Molar Selectivity (%) |
|---|---|
| Propylene Oxide | 46 |
| Acetaldehyde | 12 |
| Formaldehyde | 4 |
| Carbon Dioxide | 28 |
| Carbon Monoxide | Trace |
| Acrolein | Trace |
| Acetone | 2 |
| Allyl Alcohol | 1 |
| 1,5-Hexadiene | 1 |
| Ethylene, Ethane, and Methane | 4 |
| Other | 1 |

The results presented in Table IX above indicate that the pressure of sodium hydroxide provides an enhanced selectivity to propylene oxide of 46 percent.

What is claimed is:

1. A process for producing an alkylene oxide or mixture of alkylene oxides by a reaction which comprises reacting an olefin having from 3 to 6 carbon atoms per molecule, or mixture thereof, with an oxygen-containing gas, said olefin and said oxygen-containing gas being gaseous reactants, by contacting said gaseous reactants with a bath, stream, spray or mist of at least one molten nitrate salt catalyst, in the absence of a co-catalyst, said catalyst being present in an amount sufficient to absorb any heat generated during said reaction while maintaining an essentially constant reaction temperature, said reaction being conducted at a reaction temperature of between about 135° C. and about 600° C. and a reaction pressure of between about 1 and about 40 atmospheres.

2. The process of claim 1 wherein said reaction is effected at a pressure of between about 5 and about 25 atmospheres of pressure.

3. The process of claim 1 wherein said molten nitrate salt is selected from the group consisting of sodium, potassium, lithium, cesium, magnesium, and calciium molten nitrate salts and mixtures thereof.

4. A method for producing an alkylene oxide from an olefin having from 3 to 6 carbon atoms per molecule or mixture thereof, which comprises bubbling gaseous reactants consisting of an oxygen-containing gas and said olefin, or mixture thereof, through a bath of at least one molten nitrate salt catalyst, in the absence of a co-catalyst, said catalyst being present in an amount sufficient to absorb any heat generated during said reaction while maintaining an essentially contant reaction temperature, said reaction being conducted at a reaction temperature of between about 135° C. and about 600° C. and a reaction pressure of between about 1 and about 40 atmospheres.

5. The method of claim 4 wherein said oxygen-containing gas is fed into said bath by means of a first tube and wherein said olefin, or mixture thereof is fed into said bath by means of a second tube.

6. The method of claim 5 wherein said first tube and said second tube are co-axially mounted with respect to each other.

7. The process of claim 1 wherein said oxygen-containing gas is air and said olefin is propylene.

8. The process of claim 4 wherein said air is employed in an amount of between about 5 and about 75 volume percent based upon the total amount of air plus propylene employed in said reaction.

9. The process of claim 1 wherein said oxygen-containing gas is oxygen and said olefin is propylene.

10. The process of claim 9 wherein said oxygen is employed in an amount of between about 1 and about 20 volume percent based on the total amount of oxygen plus propylene empolyed in said reaction.

11. The process of claim 1 wherein said molten nitrate salt consists essentially of a mixture of sodium nitrate and potassiuim nitrate.

12. The process of claim 11 wherein said mixture contains between about 20 and about 80 weight percent sodium nitrate based upon the total amount of sodium nitrate plus potassium nitrate.

13. The process of claim 1 wherein said molten nitrate salt consists essentially of potassium nitrate.

* * * * *